(12) United States Patent
Hua (10) Patent No.: US 7,579,183 B1
(45) Date of Patent: Aug. 25, 2009

(54) **SAPROPHYTIC YEAST, *PICHIA ANOMALA***

(75) Inventor: Sui-Sheng T. Hua, Orinda, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 222 days.

(21) Appl. No.: 11/607,713

(22) Filed: Dec. 1, 2006

(51) Int. Cl.
*C12N 1/16* (2006.01)
*A01N 63/00* (2006.01)
*A01N 63/04* (2006.01)

(52) U.S. Cl. ..................... 435/255.2; 435/938; 504/117

(58) Field of Classification Search ........................ None
See application file for complete search history.

(56) References Cited

FOREIGN PATENT DOCUMENTS

WO    WO 97/45787    *    9/1999

OTHER PUBLICATIONS

Commission of the European Community. "Commission Directive 98/53/EC laying down the sampling methods and the methods of analysis for the official control of the levels for certain contaminants in foodstuffs" (Jul. 1998) Official Journal of the European Community L201/93-101.
Buck, J.W., "Combinations of Fungicides with Phylloplane Yeasts for Improved Control of *Botrytis cinerea* on Geranium Seedlings," Phytopathology (2004) 94(2): 196-202.
Cotty, P.J., P. Bayman, D.S. Egel, and K.S. Elias, "Agriculture, Aflatoxins and *Aspergillus*," In: The Genus *Aspergillius*, (1994) (Eds) K.A. Powell, A. Renwick, and J.F. Perberdy, Plenn Press, New York pp. 1-21.
Diener, U.L., et al., "Epidemiology of Aflatoxin Formation of *Aspergillus flavus*," Annual Review Phytopathology (1987) 25:249-270.
Ellis, W.O., J.P. Smith, and B.K. Simpson, "Aflatoxins in Food: Occurrences, Biosynthesis, Effects on Organisms, Detection, and Methods of Control," Critical Reviews in Food Science and Nutrition (1991) 30 (3):403-439.
Hua, S.-S., J.L. Baker, and O.K. Grosjean, "Improvement of the Quality and Value of Pistachios and Almonds Through Preharvest Biocontrol of *Aspergillus flavus*," In: Proceeding of the International Symp. on Pistachios and Almonds (1998) (Eds) L. Ferguson and D. Kester—Acta Horticulturae No. 470, Int. Soc. for Horticultural Science, Leuven, Belgium.
Hua, S.-S. T., J.L. Baker and M. Flores-Espiritu, "Interactions of Saprophytic Yeasts with a nor Mutant of *Aspergillus flavus*," Applied and Environmental Microbiology (1999) 65(6):2738-2740.
Hua, S., "Biocontrol Approach to Reduce *Aspergillus flavus* Population in Tree Nut Orchards," In: Proceedings of California Conference on Biological Control (2000) (Ed) M.S. Hoddle—University of California, Riverside.
Hua, S.-S. T., "Potential Use of Saprophytic Yeasts to Control *Aspergillus flavus* in Almond and Pistachio Orchards," In: Proceedings of the Third International Symposium of Pistachios and Almonds (2002) (Eds) I. Battle, I. Hormaza, and M. T. Espiau—Acta Horticulture, No. 591 Int. Society for Horticultural Science, Leuven, Belgium.
Hua, S.-S. T., "Application of a yeast, *Pichia anomala* strain WRL-076 to control *Aspergillus flavus* for reducing aflatoxin in pistachio and almond," Biological Control of Fungal and Bacterial Plant Pathogens, Jun. 9-12, 2004, Trentino, Italy. IOBC Bulletin: 27(8): 291-294.
Hua, S.-S. T., S. Kuang, L. Chang, and K. Bundy-Mills, "Identification of Fungal and Yeast isolates from Almond and Pistachio Orchard by Analysis of Nuclear Large Subunit (26S) Ribosomal DNA Sequences," In: Proceedings of Aflatoxin and Fumonisin Elimination Workshop, Sacramento, CA. Oct. 24-28, 2004.
Janisiewics, W.J., and L. Korsten, "Biological Control of Postharvest Diseases of Fruits," Annual Review Phytopathology (2002) 40:411-441.
Payne, G.A., "Aflatoxin in Maize," Critical Reviews in Plant Sciences (1992) 10(5):423-440.
Wilson, C.L. and M.E. Wisniewski, "Biological Control of Postharvest Diseases of Fruits and Vegetables: An Emerging Technology," Annual Reviews Phytopathology (1989) 27:425-441.
Hua, S.-S. T., "Biocontrol of *Aspergillus flavus* by Saprophytic Yeast: Progress from Laboratory Bioassay to Field Trial," Proceedings of the 3rd Fungal Genomics, 4th Fumonisin, and 16th Aflatoxin Elimination Workshops (Oct. 13-15, 2003) p. 85.

* cited by examiner

*Primary Examiner*—Vera Afremova
(74) *Attorney, Agent, or Firm*—Howard V. Owens; Leslie Shaw; John Fado (57) ABSTRACT

A biologically pure culture of a yeast of the species *Pichia anomala* (WRL-076). The yeast is identified as NRRL Y-30842 and is capable of inhibiting growth of a deleterious microorganism on a plant or portion thereof to which a biologically effective amount of a culture of the yeast is applied. Further disclosed is a composition for use in protection of agricultural crops.

23 Claims, 9 Drawing Sheets
(1 of 9 Drawing Sheet(s) Filed in Color)

Water activity is adjusted to 0.96 by adding PEG 8000 to the growth medium

SEQUENCE LISTING

<160> NUMBER OF SEQ ID NOS: 1

<210> SEQ ID NO 1
<211> LENGTH: 574
<212> TYPE: DNA
<213> ORGANISM: Pichia anomala WRL-076

<400> SEQUENCE: 1
ccacagggat tgcctcagta cggcgactga agcggcaaaa gctcaaattt gaaatctagc 60
accttcggtg ttcgagttgt aatttgaaga tggtaacctt gggtttggct cttgtctatg 120
ttccttggaa caggacgtca tagagggtga gaatcccgtc tgatgagatg cccattccta 180
tgtaaggtgc tatcgaagag tcgagttgtt tgggaatgca gctctaagtg ggtggtaaat 240
tccatctaaa gctaaatatt ggcgagagac cgatagcgaa caagtacagt gatggaaaga 300
tgaaaagaac tttgaaaaga gagtgaaaaa gtacgtgaaa ttgttgaaag ggaagggcat 360
tagatcagac ttggtgtttt acgattatct tctcttcttg agttgtgcac tcgtatttca 420
ctgggccagc atcgattcgg atggcaagat aatggcagtt gaatgtggct tcacttcggt 480
ggagtgttat agcttctgct gatattgcct gtctggatcg agggctgcgt cttttgacta 540
ggatgctggc gtaatgatct aatgccgccc gtcg 574

SAPROPHYTIC YEAST, *PICHIA ANOMALA*

SUMMARY OF THE INVENTION

According to an embodiment of the invention is a biocontrol agent comprising *Pichia anomala* WRL-076. Preferably the biocontrol agent comprises *Pichia anomala* WRL-076 deposit number NRRL Y-30842.

A further embodiment of the invention is a biologically pure culture of a yeast of the species *Pichia anomala* WRL-076 deposit number NRRL Y-30842, or composition thereof, the culture capable of competitively inhibiting growth of a deleterious micro-organism on an agricultural crop to which a biologically effective amount of the culture is applied. *Pichia anomala*, is referred to herein as strain WRL-076.

A further embodiment of the invention is a composition comprising the biocontrol agent WRL-076 and a carrier. Any carrier that permits the biocontrol agent to be delivered to a target plant in a manner such that the biocontrol agent remains viable and pathogenic may be employed in the composition.

A further embodiment is a method of using *Pichia anomala* to inhibit aflatoxin producing microorganisms on affected agricultural crops.

According to still further features in the described embodiments, the portion of a plant is selected from the group consisting of a stone fruit, a pome fruit, a citrus fruit, grapes, a vegetable, a flower bulb, an herb, a grain, a root, a leaf, a grain and berries.

According to further embodiments the yeast is supplied in an active or dormant physiologic state.

According to still further features in the described preferred embodiments the yeast is supplied in a physical form selected from a liquid suspension, an emulsion, a powder, granules, a lyophylsate and a gel.

According to still further features in the described embodiments the chemical antibiotic is a fungicide or an antimicrobial agent or a pesticide.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

DETAILED DESCRIPTION OF THE INVENTION

The present invention is of a new yeast species *Pichia anomala* which can be applied to agricultural produce to reduce pre-harvest and postharvest decay via competitive inhibition of a wide range of micro-organisms.

Statement of Deposit

A biologically pure culture of *Pichia anomala* was deposited May 9, 2005 under terms of the Budapest Treaty with the Agricultural Research Service Culture Collection (NRRL) National Center for Agricultural Utilization Research, Agricultural Research Service, U.S. Department of Agriculture, 1815 North University Street, Peoria, Ill. 61604 USA and given the accession number NRRL Y-30842. The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any isolate having the identifying characteristics of strains NRRL Y-30842, including subcultures and variants thereof which have the identifying characteristics and activity as described herein are included.

Specifically, the present invention can be used to reduce the incidence and/or severity of bacterial and fungal pathogens of nuts, grapes, citrus fruit, pome fruit, stone fruit, strawberries, flower bulbs, vegetables, roots, grains, foliage, and herbs.

"Grapes", as used in this specification and the accompanying claims, includes table grapes and wine grapes.

"Citrus fruit", as used in this specification and the accompanying claims, includes, but is not limited to, oranges, grapefruit, tangerines, clementines, lemons, limes, kumqwat, citroen, pomello, mandarin and hydrids derived therefrom.

"Pome fruit", as used in this specification and the accompanying claims, includes, but is not limited to, apples, pears and quinces.

"Stone fruit", as used in this specification and the accompanying claims, includes, but is not limited to, peaches, plums, nectarines, apricots, mangos.

"Nuts" as used in this specification and the accompanying claims, includes, but is not limited to tree nuts, such as, almonds, Brazil nuts, cashews, hazelnuts, macadamias, pecans, pine nuts, pistachios and walnuts; as well as peanuts.

For purposes of this specification and the accompanying claims the terms "inhibiting" and "inhibition" refer to retardation or delay of a process. As such, inhibition may be deemed to occur if the process occurs at a reduced rate as a result of application of a claimed yeast, a composition containing such a yeast, or as a result of practice of a claimed method.

A further embodiment of the invention is of methods of use of the claimed yeast, compositions containing the claimed yeast and articles of manufacture including those compositions.

The principles and operation of protection of agricultural produce against unwanted decay via competitive inhibition according to the present invention may be better understood with reference to the figures and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to another embodiment of the invention there is provided a biologically pure culture of a yeast of the species *Pichia anomala* identified as NRRL Y-30842. This culture is capable of competitively inhibiting growth of a wide range of deleterious micro-organisms on a portion of a plant to which a biologically effective amount of the culture is applied. A further embodiment is the use of the invention to combat a deleterious micro-organism on an agricultural crop or portion thereof, the method includes applying at least one time an agriculturally effective amount of a biologically pure culture of a yeast of the genus.

Any biologically pure strain of *Pichia anomala*, whether physically derived from the original deposit or independently isolated, is part of the present invention so long as it possesses all of the identifying characteristics of NRRL Y-30842. This includes biologically pure mutants of *Pichia anomala*, so long as they retain all of the identifying characteristics of NRRL Y-30842. For purposes of this specification and the accompanying claims, the term "mutant" includes both naturally occurring mutations and purposeful genetic modifications such as introduction of point mutations, plasmids, phages, phagemids, cosmids and artificial chromosomes.

The deleterious micro-organism which WRL-076 protects against include, but are not limited to, plant fungal pathogens found in, *Aspergillus* spp. including *flavus* and *parasiticus*, *Penicillium digitatum*, *Penicillium italicum*, *Penicillium expansum*, *Geotrichum candidum*, *Rhizopus stolonifer*, *Alternaria* spp., *Molinilia* spp, and *Fusarium* spp; *Botrytis* spp. as well as plant bacterial pathogens found in *Erwinia* spp., *Burkholderia cepacia* complex—(*B. cepacia* genomovar-I, III & VI; *B. vietnamiensis*, *B. multivorans*, *B. pyrrocinia*, *B. stabilis*, *B ambifaria*), *Pseudomonas* spp., *Erwinia* spp., *Ralstonia* spp., *Rhizobium* spp., *Agrobacterium* spp.

The yeast of the composition may be supplied in any physiologic state such as active or dormant. Dormant yeast may be supplied, for example, frozen (e.g in DMSO/glycerol), dried or lyophilized. Further, the yeast of the composition may be supplied in any physical form including, but not limited to a liquid suspension, an emulsion, a powder, granules, a lyophylisate or a gel.

The composition may be applied as spray or drench or as an aerosolized powder or ointment. If the composition includes dormant yeast, they may require re-activation prior to use, for example by rehydration and or incubation in a nutrient medium. Preferably, dormant yeast will become active when applied or subsequent to application.

Production and Formulation of Biocontrol Yeast, *Pichia anomala* WRL-076

Both complex media such as NYDB (nutrient broth, 10 g, yeast extract, 8 g, dextrose 10 g per liter of water), PDB (potato dextrose broth) and ME (malt extract) and chemically defined media supplemented with a variety of carbon source such as glucose, sucrose, sorbitol, molasses etc. can be used to produce *P. anomala* by fermentation. Yeast cells will be harvested by centrifugation. The resulting yeast paste (wet biomass) will be preserved by adding salt, glycerol, lactose, trehalose, sucrose, amino acids to prolonged shelve-life during storage.

Application of the yeast in liquid or suspension form may be accomplished by ground or aerial spraying using equipment routine to one of skill in the art. The nozzle of the sprayer may be adjusted for size by one of skill in the art to accommodate the size of the crop as well as the use of presently disclosed adjuvants and carriers.

A dry formulation of yeast, *P. anomala* WRL-076, can be produced by several drying methods including freeze drying, air drying, spray drying, or fluidized bed drying. Skim milk, sucrose, lactose etc., will be added to the yeast cells as protectants during the drying process. Corn meal, wheat flour, cotton meal, clay etc., will be used as carriers. The viability of formulated yeast cells will be monitored monthly up to one year.

Adjuvants may be used to increase the biocontrol activity of *P. anomala* during field application. These include surfactants such as Tween 80, BREAK THRU™; adhesion promoters such as sodium alginate, carboxymethylcellulose and chitosan; UV protectant such as solubilized lignin solution.

Potential use of *Pichia anomala* in Post-Harvest Situations.

The biocontrol yeast, *P. anomala* WRL-076 can be incorporated in wax, shellac, food grade additives to be applied to harvested fruits to protect fruits from rot during storage. The biocontrol yeast can also be used in stored grains such as wheat, corn and barley to prevent mycotoxin contamination during storage. In addition *P. anomala* WRL-076 can also be used in combination with *Candida oleophilia*, *Metschnikowia pulcherrima* or *Aureobasidium pullulans* etc., for both pre-harvest or post-harvest control of fungal pathogens.

In order to increase the overall efficacy of the composition, a chemical antibiotic may be further included. The chemical antibiotic may be a compatible fungicide, for example Iprodione or Thiabendazole, Imazalil, Fenhexamide, Pyrimethamil or a combination of Fludioxonyl and Cyprodinil or a chemical equivalent thereof or a combination including same. Alternately, or additionally, the chemical antibiotic includes an antimicrobial agent or a pesticide.

*P. anomala* can be grown on any suitable solid or in liquid media. Solid media that can be used include nutrient-yeast extract-dextrose agar, V-8 agar, and malt extract agar. The strain may be grown in liquid media in any conventional shake flask at 28° C. on a shaker at about 150-200 rpm. For larger scale operations, it is convenient to grow the culture in a fermentation tank, while applying agitation and aeration to the inoculated liquid medium. The yeast cells are harvested by conventional sedimentary methodology, e.g., centrifugation or filtering. The cultures are stored at about 4° C. until use. Yeast stock culture was maintained on potato dextrose agar (PDA). Long term storage of yeast culture was carried out in 30% glycerol at −20° C.

*P. anomala* is useful to control pre-harvest and post-harvest fungal and bacterial pathogens in agricultural crops or commodities. For purposes of the invention, control means that the fungal growth and spore production is reduced or prevented. The commodities and crops include but are not limited to nuts, figs, wheat, cotton and corn. The strain can also be applied in fruits such as apples, pears, cherries, peaches, plums, berries, grapes and strawberries for both pre-harvest and post-harvest protection.

The yeast, P. anomala WRL-076 can be mixed with any agriculturally acceptable carrier. As used in this specification and the accompanying claims, the term "carrier" refers to any substance or diluent that does not cause significant irritation to agricultural produce or plants and does not abrogate the biological activity and properties of the administered active ingredient. As such, the term specifically includes, but is not limited to, inert solvents, aqueous solutions such as culture media, inert powders or solid carriers such as clay, alginate and diatomaceous earth.

Where the strain is applied as a suspension, the suspension may optionally contain conventional additives such as surfactants, wetting agents, and antioxidants. The yeast cells are applied in an effective amount. For the purposes of this invention, an effective amount is defined as that quantity of microorganism cells sufficient to inhibit the development of the targeted pathogens. Typically, a concentration range from about $1 \times 10^6$ to $1 \times 10^9$ colony forming units (CFU)/ml is effective. The preferred concentration range is from $1 \times 10^7$ to $1 \times 10^8$ CFU/ml. The yeast cells can be applied in water, physiological buffer, or in mixtures with lower rates of fungicides for control of pathogens.

The invention is further embodied by an article of manufacture which includes packaging material and a composition identified for use in protection of agricultural produce from a deleterious micro-organism. The article of manufacture includes, as an active ingredient, a biologically effective amount of yeast of biologically pure *Pichia anomala* and further contains a carrier. Preferably, the article of manufacture further includes an applicator designed and constructed to apply the yeast to the agricultural produce.

The claimed yeast species, compositions and articles of manufacture including same and methods of use thereof are expected to find great utility in commercial agriculture. Their utility stems from their broad spectrum of activity against important pathogens and from the wide range of plants/fruits to which they may be efficaciously applied. In addition, P. anomala may be applied in the field, or concurrent with harvest, or during storage. Further, as demonstrated in examples herein below, P. anomola is useful under a wide variety of storage conditions. Thus, an embodiment of the invention allows pre-harvest application of benign yeast as a means of preventing post-harvest decay of agricultural produce.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed below finds experimental support in the following examples.

EXAMPLES

Two hundred strains of yeasts were isolated from the external surfaces of buds, twigs, leaves, fruits, nuts of pistachio and almond (tree and ground sources). Plant samples were transferred to a flask containing Tween-80 water (0.05% Tween 80), followed by vortexing and shaking, ultrasound has also been employed to facilitate the dislodgement of higher numbers of yeasts species. The microbial suspension was plated on nutrient agar media. Yeast colonies were purified by streaking each single colony on agar medium.

Figure 1:
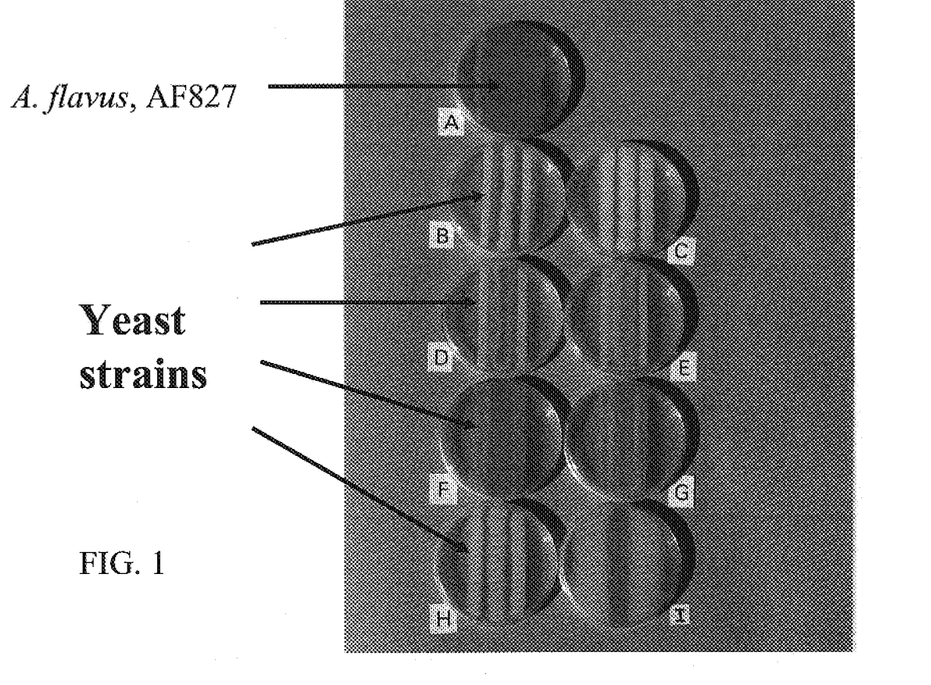
FIG. 1. is a photo of the efficacy of yeast species antagonistic to *Aspergillus flavus*. A nor mutant of *A. flavus* Papa 827 is used as an indicator strain for visual monitoring. (A) nor mutant in the absence of yeast; (B) to (G), different species of yeasts are applied to the agar plates as follows: WRL-076, WRL-038, WRL-084, WRL-015, WRL-024 and WRL-053.

A visual bioassay was developed to screen for antagonistic activity against *Aspergillus flavus*, Papa 827 as well as other isolates of *A. flavus*. We used the following bioassay protocol: (i) the yeast isolate was grown in a flask containing potato dextrose broth (DIFCO™) for 24 h on a shaker at 28° C., and the fresh culture was used for inoculation; (ii) spore suspensions of the nor mutant were prepared ($10^4$ spores/ml); (iii) two streaks of 20-μl yeast cultures were applied 15 mm from the center line of a petri dish containing PDA; (iv) 4 h later, 20 μl of the *A. flavus* spore suspension was inoculated along the center line of the PDA agar; (v) the petri dish was sealed with Parafilm M (American National Can, Neenah, Wis.) and incubated at 28° C. for 10 days. We determined the effects of yeast isolates on *A. flavus* by visually estimating the amount of red-orange color formed by the nor mutant (FIG. 1). A score of ++++was assigned to the bright orange pigment level of control (FIG. 1A), and a score of – was assigned to an almost imperceptible level of pigment (FIGS. 1B and C). The growth of the nor mutant was restricted to and reduced within the boundary of the two streaks of the yeast zone in the bioassay (FIG. 1). As shown in FIG. 1, the fungal colony expanded toward the edges of the PDA in the petri dish in the absence of the yeasts as shown in FIG. 1. The visual bioassay described here provides a simple and useful monitoring system for screening large numbers of yeast strains for their effectiveness in blocking early steps of the polyketide pathway in the biosynthesis of aflatoxin by *A. flavus*. The nor mutant also is safer for use in routine experiments than is a wild-type strain of *A. flavus*, since the mutant produces little if any aflatoxin during routine laboratory culture.

Two hundred strains of yeasts were screened for their potential to prevent the growth of *A. flavus* by a visual bioassay. A few species of yeasts have been identified to be effective in inhibiting both the growth of *A. flavus* and aflatoxin production (Hua, et al., 1998, Hua et al., 1999). One isolate, WRL-076 was effective in inhibiting both the growth and aflatoxin production of *A. flavus*. The yeast were identified to be *Pichia anomala* by Central Bureau for Fungal Culture (CBS), Baarn, the Netherlands, based on morphological characteristics, fermentation of sugars, and growth on different carbon and nitrogen sources.

The biocontrol efficacy of a strain of yeast, P. anomala WRL-076, was evaluated further on pistachio flowers, leaves, nut-fruits and almond leaves. Spore production of *A. flavus* was reduced by about 80% in pistachio flowers sprayed with the yeasts. It was also effective in decreasing spore production by 40-60% on almond and pistachio leaves sprayed with P. anomala WRL-076. Wounded pistachio nut fruits inoculated with yeast decrease spore production of *A. flavus*. Almond nuts sprayed with the yeast showed much less fungal growth.

Figure 2:
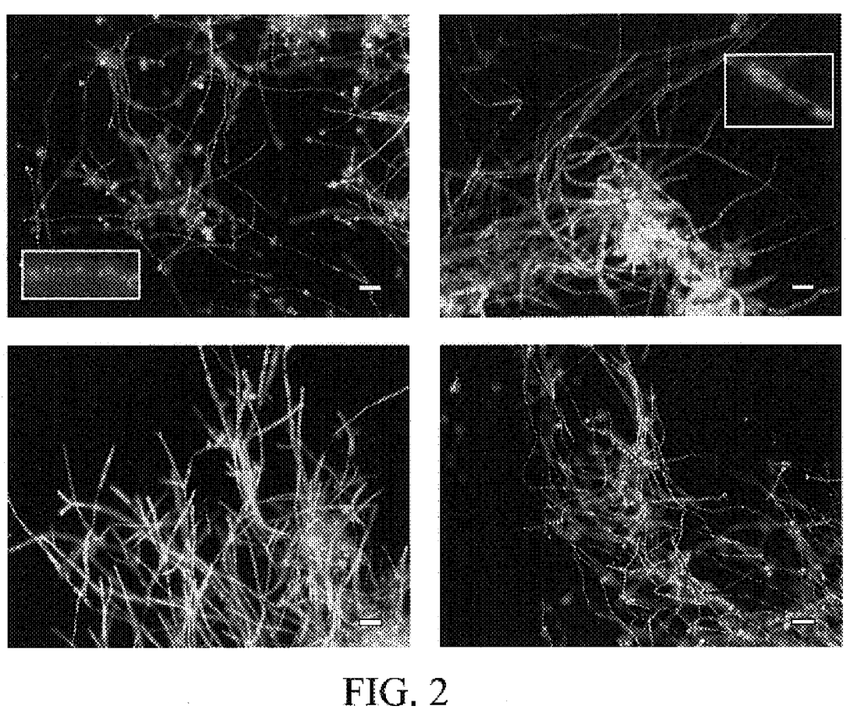
FIG. 2. is a photo of epifluorescence micrographs of live, yeast treated, and heat killed *Aspergillus flavus* stained with FUN-1 viability stain. Metabolically active *A. flavus* hyphae accumulated red fluorescence in vacuoles, while hyphae that were inhibited by *P. anomala* WRL-076 stained green.
Figure 3:
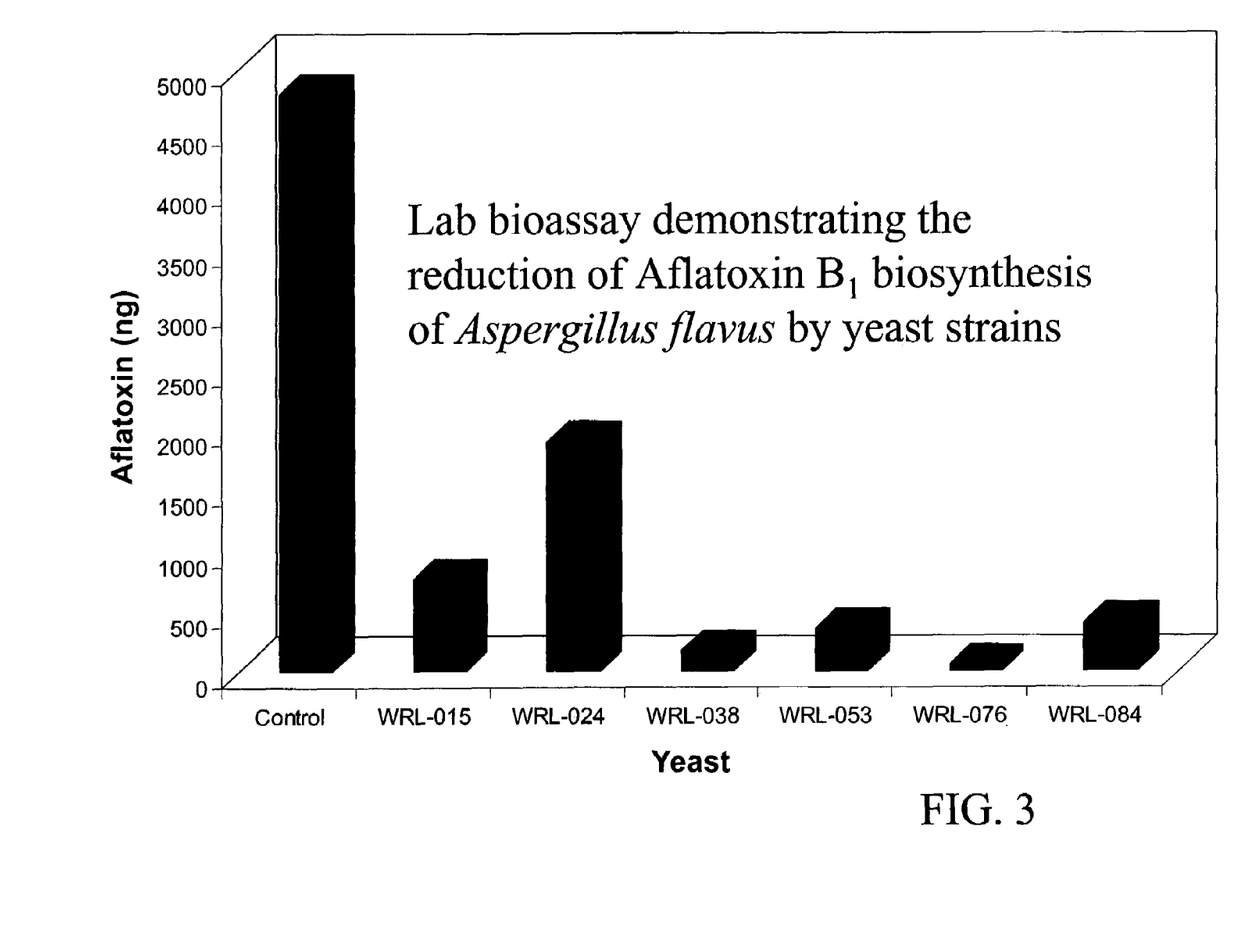
FIG. 3. is a graph of the effects of different yeast species on aflatoxin production by a toxigenic strain of *Aspergillus flavus* 42-12.
Figure 4:
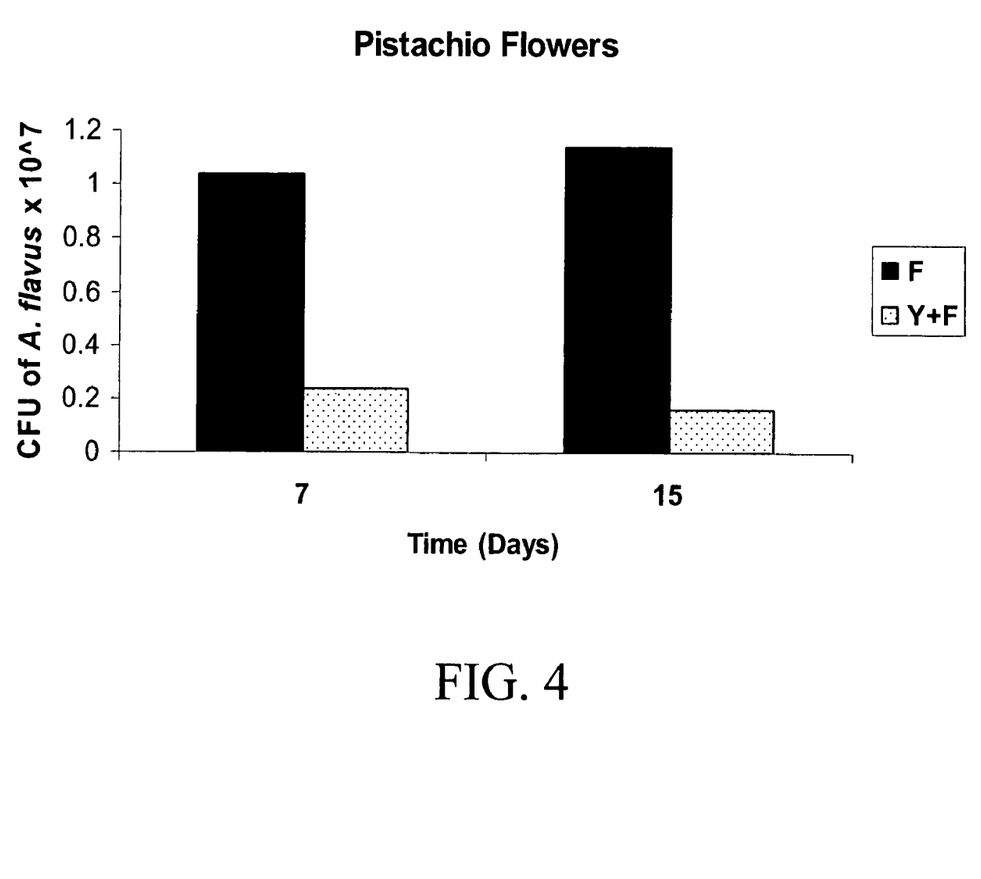
FIG. 4. is a graph of the inhibition of *Aspergillus flavus* spore production by the yeast, *Pichia anomala* WRL-076. Pistachio flowers were used as the experimental materials. Viable spores were determined by counting clony forming units (CFU) on nutrient agar.
Figure 5:
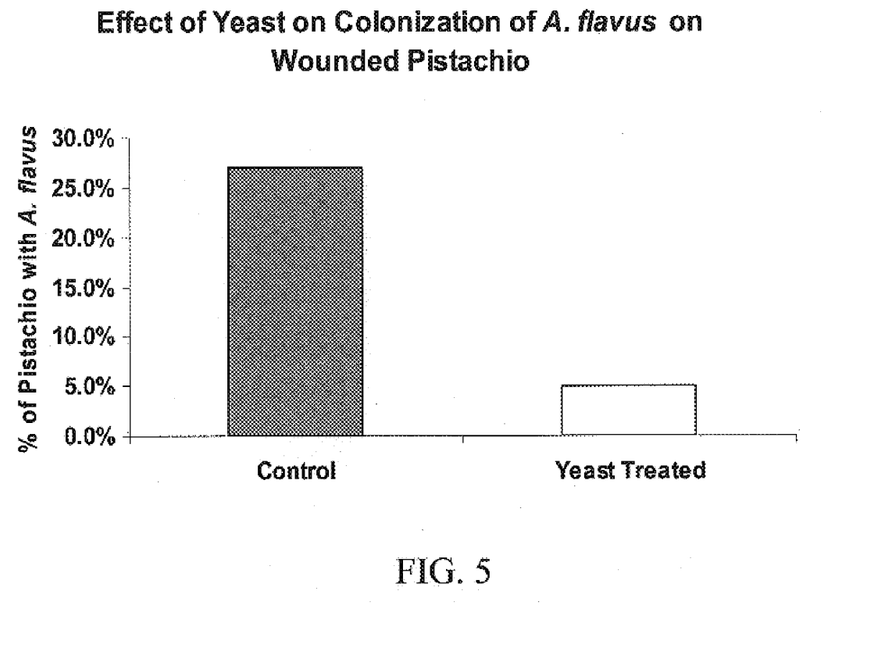
FIG. 5. is a graph of the effect of yeast on colonization of *Aspergillus flavus* on wounded pistachio nut-fruits.
Figure 6:
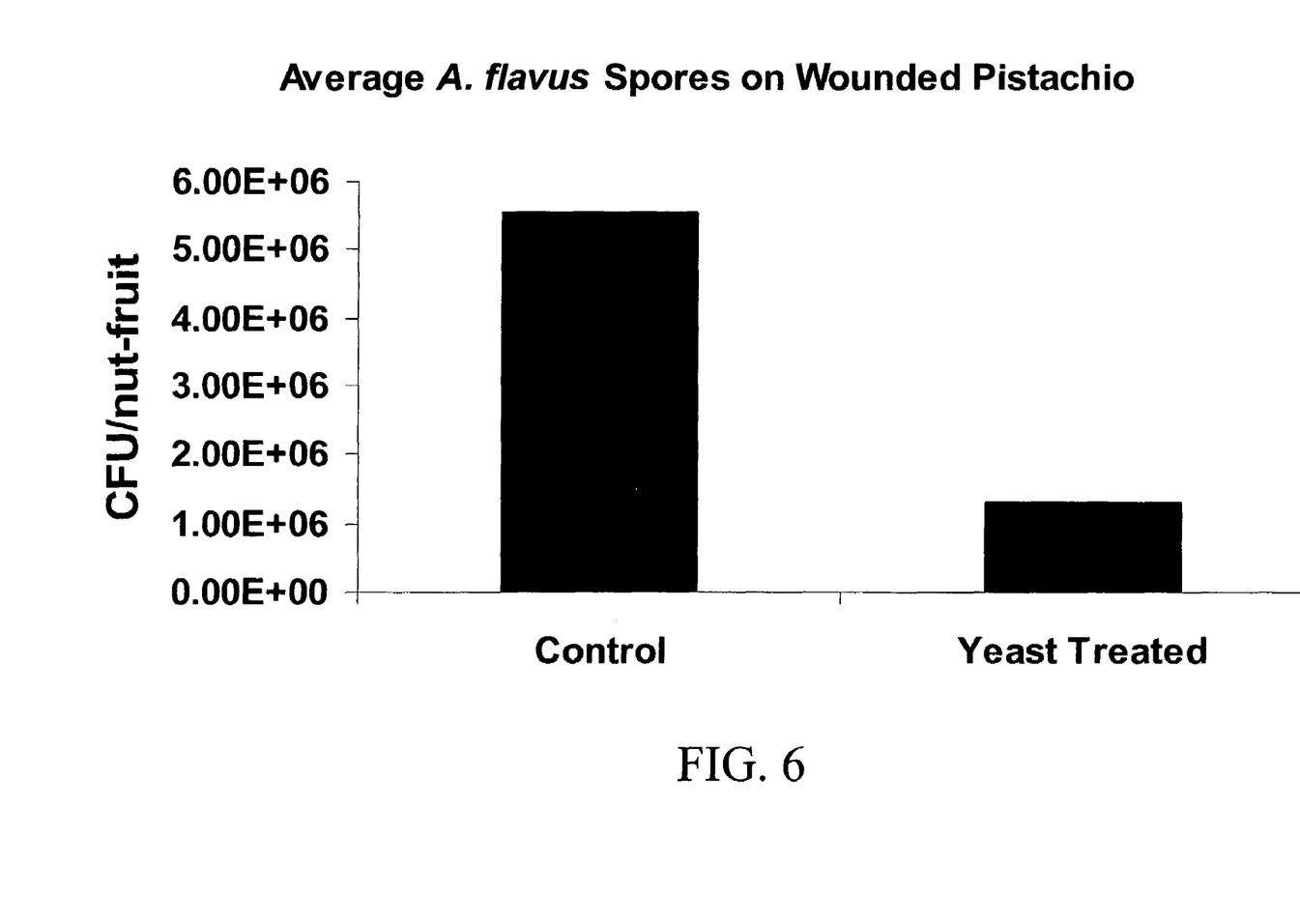
FIG. 6. is a graph of the reduction of *Aspergillus flavus* spores by yeast on wounded pistachio nut-fruits. Spores were enumerated by plating the samples on nutrient agar plates.
Figure 7:
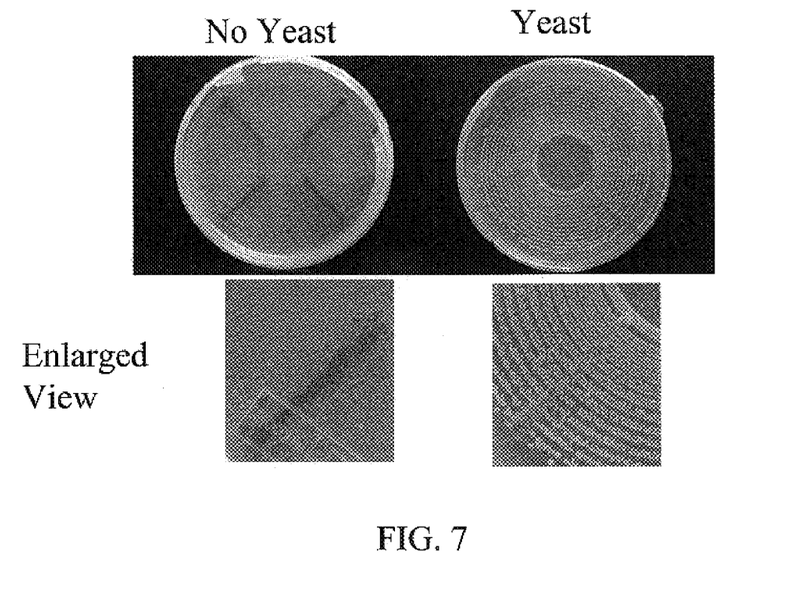
FIG. 7. is a photo of the biocontrol of *Aspergillus flavus* isolated from corn kernels by *Pichia anomala* WRL-076.
Figure 8:
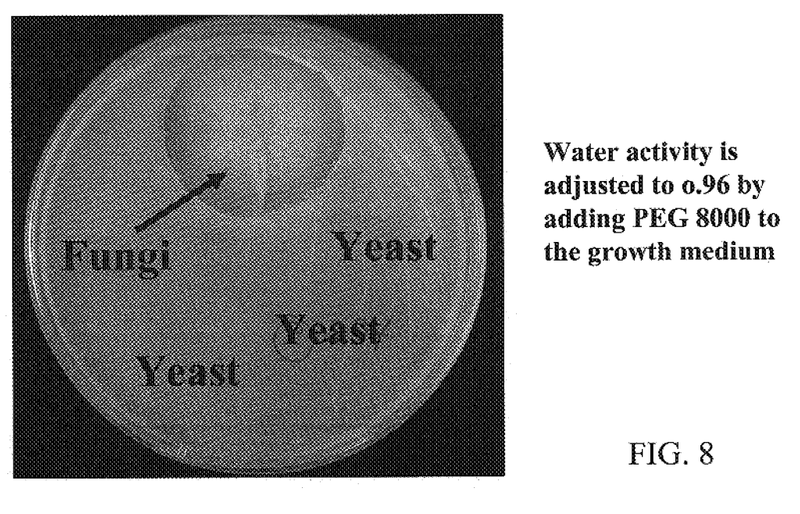
FIG. 8. is a photo of the biocontrol of *Aspergillus flavus* by *Pichia anomala* WRL-076 at low water activity. Polyethylene glycol 8000 was used to adjust the water in the medium.

FUN-1 [2-chloro-4-(2,3 dihydro-3-methyl (benzo-1,3-thiozol-2-yl)-methylidene)-1-phenylquinolinium iodide] stain is a membrane-permeant, halogenated cyanine compound that binds nucleic acids and has an unique and useful property. FUN-1 stain was used to assess damage of hyphae by antifungal agents in several species of *Aspergilli* (Lass-Florl et al, 2001; Marr et al, 2001; Balajee et al., 2002). These studies show that FUN-1 is useful as a viability stain to monitor the metabolic status of yeast and fungi. FUN-I was used to visualize the metabolic status of *A. flavus* grown in the presence or absence of the biocontrol yeast in potato dextrose broth. Metabolically active *A. flavus* hyphae accumulated red fluorescence in vacuoles, while hyphae that were inhibited by P. anomala WRL-076 stained green. Red fluorescence accumulation in the vacuoles was greatly reduced in *A. flavus* hyphae when the yeast to fungus ratio was 50 (FIG. 2).

The yeast, WRL-76 was identified as *Pichia anomala* (E. C. Hansen) Kurtzman according to standard procedures. Characteristics are: fermentation is present; cells are pink colored, lemon-shaped; Pseudo hyphae are visible from colony margins. Additional information regarding growth characteristics of isolates *Pichia anomala* WRL-076 is given below:

| WRL-076 | |
|---|---|
| D-glucose | + |
| D-galactose | v |
| L-sorbose | − |
| D-glucosamine | − |
| D-ribose | − |
| D-xylose | − |
| L-arabinose | − |
| L-rhamnose | − |
| sucrose | + |
| maltose | + |
| trehalose | + |
| methyl-glucoside | + |
| cellobiose | + |
| melibiose | − |
| lactose | − |
| raffinose | + |
| melezitose | − |
| glycerol | + |
| meso-erythritol | + |
| D-glucitol | + |
| D-mannitol | + |
| myo-inositol | − |
| 2-keto-D-gluconate | + |
| D-gluconate | v |
| D-glucuronate | − |
| DL-lactate | + |
| nitrate | + |
| ethylamine | + |
| lysine | + |
| cadaverine | + |
| growth at 25.degree. C. | + |
| growth at 30.degree. C. | + |
| growth at 37.degree. C. | poor |

DNA sequence analysis of large subunit ribosome using the universal primer pair, NL1 and NL2 shows that *P. anomala* WRL-076 has the following sequences:

CCACAGGGATTGCCTCAGTACGGCGACTGAAGCGGCAAAAGCTCAAATTT

GAAATCTAGCACCTTCGGTGTTCGAGTTGTAATTTGAAGATGGTAACCTT

GGGTTTGGCTCTTGTCTATGTTCCTTGGAACAGGACGTCATAGAGGGTGA

GAATCCCGTCTGATGAGATGCCCATTCCTATGTAAGGTGCTATCGAAGAG

TCGAGTTGTTTGGGAATGCAGCTCTAAGTGGGTGGTAAATTCCATCTAAA

GCTAAATATTGGCGAGAGACCGATAGCGAACAAGTACAGTGATGGAAAGA

TGAAAAGAACTTTGAAAAGAGAGTGAAAAAGTACGTGAAATTGTTGAAAG

GGAAGGGCATTAGATCAGACTTGGTGTTTTACGATTATCTTCTCTTCTTG

AGTTGTGCACTCGTATTTCACTGGGCCAGCATCGATTCGGATGGCAAGAT

AATGGCAGTTGAATGTGGCTTCACTTCGGTGGAGTGTTATAGCTTCTGCT

GATATTGCCTGTCTGGATCGAGGGCTGCGTCTTTTGACTAGGATGCTGGC

GTAATGATCTAATGCCGCCCGTCG

The result of Blast against GenBank data base indicate that *P. anomala* strain WR1-076 is a bona fide species of *Pichia anomala*.

Aflatoxin contamination is associated with wounding in corn, peanut, cotton seed and tree nut (Diener et al, 1987; Payne, 1992; Cotty et al, 1994; Hua et al, 1998). Assessment of the efficacy of *P. anomala* has been achieved by mechanically wounding pistachio nuts on the tree in the orchard to increase the number of wounded nuts. The results clearly demonstrate that the production of *A. flavus* spores was drastically inhibited by spraying yeast onto wounded pistachio nuts. One can anticipate that field spraying of this effective yeast to pistachio trees will decrease the population of *A. flavus* in the orchards. The outcome will be a reduction of aflatoxin contamination in the edible nuts. Using pistachio as a model system, similar results can be predicted for almond and corn.

The following examples are intended only to further illustrate the invention and are not intended to limit the scope of the invention which is defined by the claims.

EXAMPLES

Example 1

Growth Inhibition of Nor Mutant

To measure growth inhibition of the nor mutant, we determined the dry weight of the fungal mass in the agar between the two streaks of yeast. Five agar discs (7-mm diameter) of fungal mycelium were cored and transferred to boiling water. The floating mycelial mat was washed once in boiling water to remove agar traces and air dried at room temperature for 16 h. The dry weight of the fungal mass depended upon the yeast strain in the petri dish. Growth and norsolorinic acid were not correlated (r=0.43 and p=0.18 based on the Kendall correlation), so the yeasts must affect norsolorinic acid accumulation in some manner other than simply reducing the amount of biomass available to accumulate the compound.

TABLE 1

Effects of saprophytic yeasts on *Aspergillus flavus* strain Papa AF 827

| Yeast | Norsolorinic acid (□g/5 discs) | Biomass (mg/5 discs) |
|---|---|---|
| WRL-015 | 16 ± 2.1 | 7.2 ± 0.7 |
| WRL-024 | 66 ± 8.3 | 6.8 ± 0.7 |
| WRL-038 | 3 ± 0.4 | 5.5 ± 0.5 |
| WRL-053 | 60 ± 7.2 | 7.0 ± 0.6 |
| WRL-076 | 4 ± 0.8 | 3.8 ± 0.4 |
| WRL-084 | 21 ± 3.5 | 4.5 ± 0.4 |
| Control | 112 ± 12 | 8.8 ± 0.7 |

Example 2

Inhibition of Aflatoxin Biosynthesis

A toxigenic strain *A. flavus* 42-12 was used to test the effectiveness of the six yeasts for inhibiting aflatoxin biosynthesis in the bioassay. Four agar discs (7-mm diameter) of fungal cultures were cored in the center of a petri dish and transferred to a glass tube containing methanol. Aflatoxin was extracted and analyzed by high performance liquid chromatography. When grown on PDA, strain 42-12 produced 4,800 ng of aflatoxin per four discs. Aflatoxin production was drastically reduced by yeasts WRL-076 and WRL-038 and moderately reduced by WRL-015, WRL-053, and WRL-084 (FIG. 3).

Example 3

The Effect of the Yeast on the Growth of *A. flavus* was Evaluated on Pistachio Male Flowers The male flowers were collected from orchards and sterilized by autoclave. Five gram of male flowers were weighted and placed in a Petri dish. Spore suspension of *A. flavus* was prepared in Tween 80 solution (0.05%) and yeast suspension was prepared in sterile water. A Beckman-Coulter Multisizer was used to determine the number of spore and yeast. The yeast suspension was adjusted to $10^8$/ml and the spore suspension to $10^4$/ml. Samples (Y+F) were each sprayed with 2 ml of yeast suspension and incubated at 28° C. for 24 h, and then each sprayed with 2 ml of spore suspension. After the treatment, the samples were incubated at 28° C. Triplicate samples were analyzed for colony forming units (CFU) of yeast and fungal spore on day 1, day 7 and day 15.

One set of samples (Y) were each sprayed with 2 ml of yeast suspension and 2 ml of water, and then incubated at 28° C. for monitoring the growth of yeast. The number of yeast on the flowers were evaluated on day 1, day 7 and day 15. In addition, one set of samples (F) were sprayed with 2 ml of spore suspension and 2 ml of water, then incubated at 28° C. to monitor the growth of *A. flavus* in the absence of yeast and analyzed on day 1, day 7 and day 15.

Figure 9:
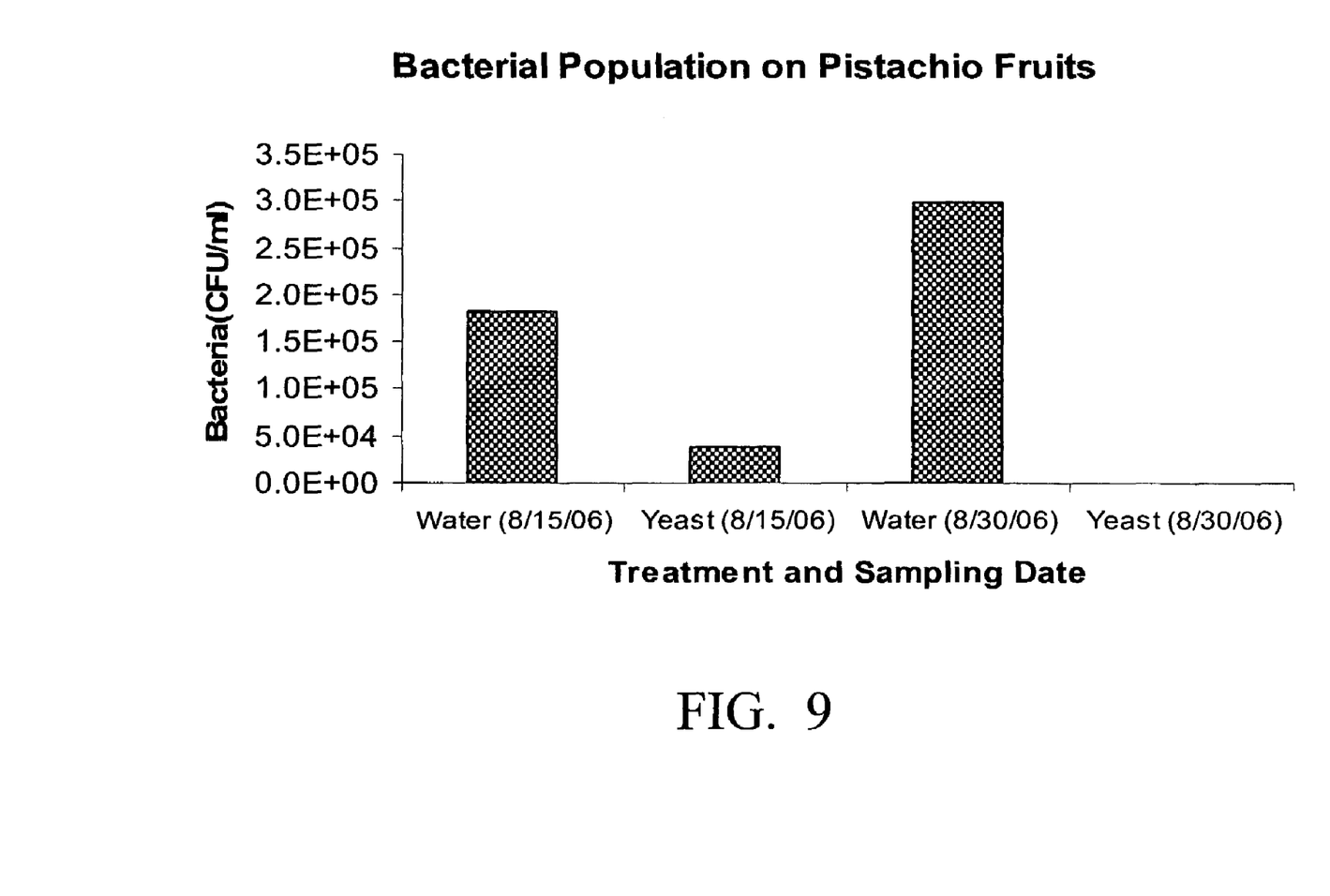
FIG. 9. is a graph of the effect of yeast on the population of *Burkholderia cepacia*. Yeast cells were sprayed to the pistachio trees. Nut-fruit samples were collected and enumerated for the number of bacteria.

Yeast and fungal spores were eluted in Tween 80 solution from the experimental samples by shaking and sonicating in flasks. A spiral plating system was used to spread the yeasts or spores onto nutrient agar. The CFU of yeast and *A. flavus* on the agar plates were counted using the spiral counting formula. FIG. 4 shows that spore production of *A. flavus* increased over a period of 15 days. In flowers sprayed with yeast, spore production was reduced by 80%.

Example 4

Field Evaluation of the Efficacy of the Biocontrol Agent, *P. anomala* WRL-076

The yeast strain, *P. anomala* WRL-076 was maintained on potato-dextrose agar (PDA, Difco, Detroit, Mich.). Yeast suspension was prepared in sterile water. A Beckman-Coulter Multisizer was used to determine the number of yeast cells. Microorganisms were eluted in Tween 80 solution from the experimental samples by shaking and sonicating in flasks. A spiral plating system was used to spread the microorganisms onto nutrient agar. Viable counts of yeast were determined by spreading the yeast on dichloran rose bengal chloramphenicol (DRBC) agar plate. Pistachio nut-fruits on the tree were individually wounded with a dental needle and sprayed with aqueous suspension of yeasts at $3\times10^7$ cells/ml in August. The wounded nut-fruits without yeast-spray were used as controls. Five weeks after the yeast spray, wounded nut-fruit was hand picked from the tree and immediately placed to a special agar medium and incubated at 28° C. for eight days. The viable fungal and yeast counts on individual nut were enumerated by standard microbiological techniques. In order to see the variation among the nuts, every single nut collected was analysed for colonization of *A. flavus* and viable spores production. The percent colonization of *A. flavus* on nut-fruits was 27.1% for the control and 5.1% for the yeast treated nut-fruits (FIG. 5). The CFU of *A. flavus* spores from each single nut was enumerated. Average spore production in *A. flavus* infected nuts was $5.6\times10^6$ and $1.3\times10^6$ (FIG. 6). The total number of *A. flavus* spores produced on wounded pistachios in the control is $1.28\times10^8$ and for yeast sprayed pistachios is $5.2\times10^6$ respectively. A 96% reduction in spore number present in the orchard environment. The experiments demonstrated that the yeast, *P. anomala* can modulate spore production of *A. flavus* on wounded pistachio nut-fruits and is very powerful in reducing the spore production of *A. flavus*. This unique biocontrol activity of *P. anomala* WRL-076 can prevent further infection of *A. flavus* to pistachio nuts during the growing season in orchards.

Example 5

Control of *A. flavus* Isolated from Corn Kernels by *P. anomala* WRL-076

Thirty five strains of *A. flavus* were isolated from corn kernels. *P. anomala* WRL-076 shows good control of these strains by the two streak bioassay, on PDA. The efficacy of the biocontrol yeast, *P. anomala* WRL-076 has also been demonstrated by using Autoplate 4000 to spread the yeast at $10^6$ cells/ml in a controlled manner exponentially onto corn meal (made of grounded corn kernels) agar. 5□l of *A. flavus* spores at $2\times10^5$/ml was pipeted onto each quarter of the agar plates in a thin line from the center towards edge of the plates (FIG. 7). The corn meal agar plate without yeast was used as the control. The inoculated plates were incubated at 28° C. for 7 days. Spore production on the agar plates were recorded by using a digital camera. The dense oliver green spores on corn meal agar can be easily visualized. In contrast the corn meal agar spread with the yeast showed very significantly less spores. The results indicate that the yeast has the potential to control *A. flavus* associated with corn.

Example 6

Control of *A. flavus* Under Water Stress

In general, antagonists applied to crops for control of foliar diseases are exposed to environmental stresses such as temperature fluctuation and water availability. In laboratory experiments, PEG (polyethylene glycol) 8000 was used to adjust medium $a_w$ to 0.96, which mimicked a water stress condition of −5.62 MPa. *P. anomala* WRL-076 could grow at this low water activity ($a_w$). Spores of *Aspergillus flavus* were inoculated at one corner of PD broth containing PEG and incubated at 25° C. for three days, then the yeast cells were inoculated at the opposite corner and incubated for additional 7 days. The yeast cells formed a film and inhibited the growth of *A. flavus* inoculated to the medium (FIG. 8).

Example 7

Inhibition of a Wide Range of Pathogenic Fungi by *P. anomala* WRL076

In addition to *A. flavus* the yeast was shown to be antagonistic to several other filamentous fungi such as *Aspergillus ochraceus, Fusarium* spp., *Penicillium spp, Botrytis cinera, Alternaria* spp by using the bioassays developed for *A. flavus*. Some of these pathogenic fungi produce mycotoxins such as ochratoxin, fumonisin, patulin etc., which are harmful to animal and human health.

Example 8

Inhibition of Gram Negative Bacteria by *P. anomala* WRL-076

Field experiments were conducted in a commercial pistachio orchard. Trees were sprayed with yeast cells which were suspended in water. Another group of trees were sprayed with water without any yeast and used as the control. For the water treatment, a dominant bacterium species appeared on the pistachio nut fruits and leaves. The bacterium was identified as the human pathogen, *Burkholderia cepacia*, by sequencing the 16 S ribosomal PCR fragment. The source of the bacterium was found in a local water supply. Leaves and nut-fruits from trees sprayed with yeast cells had a much reduced number of the bacterium. FIG. 9 shows the bacterial population on pistachio nut-fruits for yeast treated and water treated samples. The results demonstrated that the yeast inhibited the growth of the bacterium.

7. The composition of claim 6, wherein the carrier is selected from the group consisting of a liquid, clay, alginate, diatomaceous earth, growth medium, or combination thereof.

8. The composition of claim 6, wherein said yeast is supplied in a physiologic state selected from the group consisting of active and dormant.

9. The composition of claim 6, wherein said yeast is supplied in a physical form selected from the group consisting of a liquid suspension, an emulsion, a powder, granules, a lyophylsate and a gel.

10. The composition of claim 6, further comprising a chemical antibiotic.

What is claimed is:

1. A biologically pure culture of a yeast of the species *Pichia anomala* having all of the identifying characteristics of the deposited sample identified as WRL-076 (NRRL Y-30842), said culture capable of competitively inhibiting growth of a deleterious micro-organism on a plant to which a biologically effective amount of the culture is applied.

2. The culture of claim 1, wherein the micro-organism is a fungus.

3. The culture of claim 1, wherein the micro-organism is a bacterium.

4. The culture of claim 2, wherein the fungus is selected from the group consisting of *Aspergillus* spp.

5. The culture of claim 3, wherein the bacterium is selected from the group consisting of *Erwinia* spp. and *Burkholderia cepacia* complex.

6. A composition for use in combating deleterious micro-organisms comprising, as an active ingredient, a biologically effective amount of biologically pure yeast *Pichia anomala* having all of the identifying characteristics of the deposited sample identified as WRL-076 (NRRL Y-30842), said composition containing a carrier.

11. The composition of claim 6, wherein said chemical antibiotic is selected from the group consisting of a fungicide, an antimicrobial agent and a pesticide.

12. A method of inhibiting growth of a deleterious micro-organism on a plant, the method comprising applying at least one time an biologically effective amount of a biologically pure culture of yeast *Pichia anomala* having all of the identifying characteristics of the deposited sample identified as WRL-076 (NRRL Y-30842), to a plant.

13. The method of claim 12 wherein the microorganism is a fungus.

14. The method of claim 12 wherein the microorganism is a bacterium.

15. The method of claim 14, wherein the bacterium is selected from the group consisting of *Erwinia* spp., *Burkholderia cepacia* complex—(*B. cepacia genomovar*-I, III & VI; *B. vietnamiensis, B. multivorans, B. pyrrocinia, B. stabilis, B ambifaria*), *Pseudomonas* spp., *Erwinia* spp., *Ralstonia* spp., *Rhizobium* spp., *Agrobacterium* spp.

16. The method of claim 13 wherein the microorganism is a fungal pathogen selected from the group consisting of *Aspergillus spp*, *Penicillium* spp., *Geotrichum candidum, Rhizopus stolonifer, Alternaria* spp., *Molinilia* spp, and *Fusarium* spp and *Botrytis* spp.

17. The method of claim 16 wherein the fungus is *Aspergillus flavus*.

18. The method of claim 12 wherein the plant comprises an agricultural crop.

19. The method of claim 17 wherein the crop is selected from the group consisting of cotton, corn, nuts, figs and wheat.

20. The method of claim 19 wherein the nuts are selected from the group consisting of tree nuts and peanuts.

21. The method of claim 12 wherein the application of the yeast is accomplished via spraying.

22. The method of claim 12, further comprising application adjuvants.

23. The method of claim 22, wherein the adjuvants are selected from the group consisting of surfactants, adhesion promoters, and UV protectants.

* * * * *